United States Patent
Caruso et al.

(10) Patent No.: US 9,952,125 B2
(45) Date of Patent: Apr. 24, 2018

(54) REMOTE SAMPLING BYPASS FOR A GAS ANALYSER

(71) Applicant: Draeger Safety, Inc., Pittsburgh, PA (US)

(72) Inventors: Michael V. Caruso, Beaver Falls, PA (US); Eric J. Robey, Colliers, WV (US)

(73) Assignee: Draeger Medical Systems, Inc., Andover, MA (US)

( * ) Notice: Subject to any disclaimer, the term of this patent is extended or adjusted under 35 U.S.C. 154(b) by 125 days.

(21) Appl. No.: 15/022,914

(22) PCT Filed: Oct. 11, 2013

(86) PCT No.: PCT/US2013/064686
§ 371 (c)(1),
(2) Date: Mar. 17, 2016

(87) PCT Pub. No.: WO2015/053794
PCT Pub. Date: Apr. 16, 2015

(65) Prior Publication Data
US 2016/0223436 A1    Aug. 4, 2016

(51) Int. Cl.
*G01N 1/22* (2006.01)
*G01N 33/00* (2006.01)
(Continued)

(52) U.S. Cl.
CPC .............. *G01N 1/2273* (2013.01); *G01N 1/24* (2013.01); *G01N 33/0016* (2013.01); *G01N 2021/0193* (2013.01)

(58) Field of Classification Search
CPC .................. G01N 1/2273; G01N 1/24; G01N 2021/0193; G01N 33/0016; G01N 33/00; G01N 35/02; G01N 1/22; G01N 21/78
See application file for complete search history.

(56) References Cited

U.S. PATENT DOCUMENTS

| 5,889,195 A | 3/1999 | Kaneblei |
| 6,098,523 A * | 8/2000 | Warburton ............. G01D 18/00 204/290.01 |

(Continued)

FOREIGN PATENT DOCUMENTS

EP    0316688 A2    5/1989

OTHER PUBLICATIONS

Dräger Catalog, "Dräger Gas Detection," 6 pages.

*Primary Examiner* — Francis Gray
(74) *Attorney, Agent, or Firm* — Jones Day

(57) ABSTRACT

Described herein is a gas detection system (5) including a housing (10) having an inlet (20) in fluid communication with an atmosphere; an analyzer (25) within the housing (20) and configured to detect and measure a gas species in the atmosphere using a gas sensor (37); and a pneumatic system (60) contained within the housing (10) and in fluid communication with the inlet (20) to draw an air sample from the atmosphere. The pneumatic system (60) includes a pump (15); a low flow branch (65) in fluid communication with the pump (15) and having an airflow sensor (90) and a first orifice (85); and a high flow branch (70) in fluid communication with the pump (15) and having a second orifice (95). Such a system is particularly suitable for remote sampling because it prevents the high flow needed for remote sampling to be directed towards the gas sensor withstanding only low flow. Related apparatus, systems, methods and/or articles are described.

34 Claims, 7 Drawing Sheets

(51) Int. Cl.
   *G01N 1/24*      (2006.01)
   *G01N 21/01*     (2006.01)

(56) References Cited

U.S. PATENT DOCUMENTS

| | | | | |
|---|---|---|---|---|
| 2005/0142662 | A1* | 6/2005 | Bonne | B82Y 15/00 436/149 |
| 2005/0254996 | A1* | 11/2005 | Haupt | G01N 27/622 422/606 |
| 2006/0062688 | A1* | 3/2006 | Lawrence | G01N 21/78 422/400 |
| 2009/0181411 | A1* | 7/2009 | Battrell | B01F 11/0071 435/7.92 |
| 2011/0277679 | A1* | 11/2011 | Good | G01N 1/2202 116/202 |
| 2012/0177543 | A1* | 7/2012 | Battrell | B01F 11/0071 422/187 |

* cited by examiner

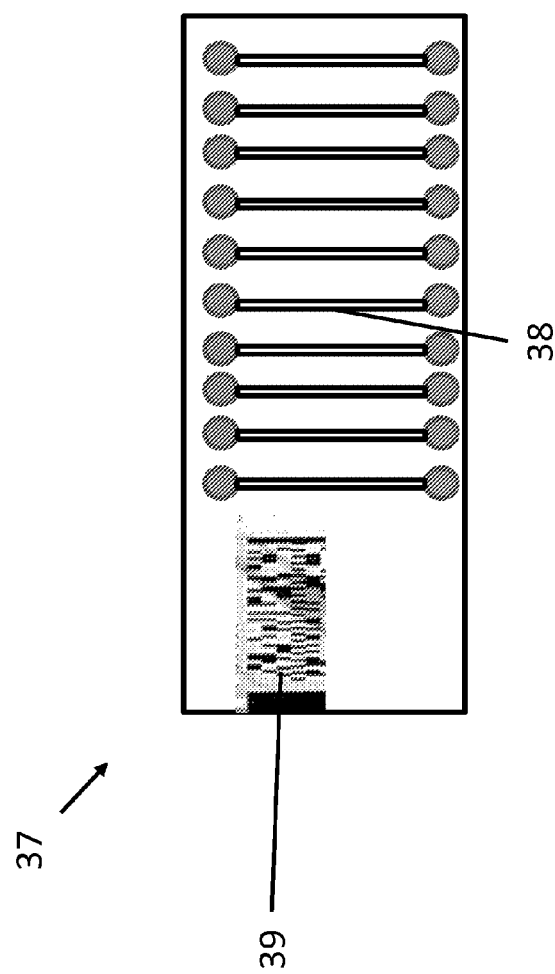

REMOTE SAMPLING BYPASS FOR A GAS ANALYSER

RELATED APPLICATION

This application is a national stage application, filed under 35 U.S.C. § 371, of International Application No PCT/US2013/064686, filed Oct. 11, 2013, the entirety of which is incorporated herein by reference.

TECHNICAL FIELD

The subject matter described herein relates to gas detection, monitoring and environmental warning systems.

BACKGROUND

A person often must be present in environments where the air is dangerous or can become dangerous due to the presence of harmful gases and toxics. When the air in the environmental atmosphere becomes dangerous to a person, such as due to high concentration of the dangerous gases, it can be necessary for the person to know that fact. Various types of gas monitoring and sensing devices are used in such environmental atmospheres.

SUMMARY

In one aspect, disclosed is a gas detection system including a housing having an inlet in fluid communication with an atmosphere; an analyzer within the housing and configured to detect and measure a gas species in the atmosphere using a gas sensor; and a pneumatic system contained within the housing and in fluid communication with the inlet to draw an air sample from the atmosphere. The pneumatic system includes a pump; a low flow branch in fluid communication with the pump and having an airflow sensor; and a high flow branch in fluid communication with the pump and having a second orifice.

The system can further include a filter upstream of the airflow sensor. The filter can be a sulfur trioxide particulate filter. The system can further include a remote sampling hose connected to the inlet. The pump can be configured to draw the air sample through the remote sampling hose using the high flow branch. The air sample can be divided into a first portion that flows through the low flow branch and a second portion that flows through the high flow branch. The first portion can flow through the gas sensor. The gas sensor can be positioned on a disposable element. A plurality of gas sensors can be positioned on the disposable element as a parallel array. The disposable element can be a planar chip. A first flow rate of the first portion and a second flow rate of the second portion can each be controlled by the low flow branch. The first flow rate can be at least about 7.5 mL/minute, 10 mL/minute, 12.5 mL/minute, 15 mL/minute, 20 mL/minute, or 50 mL/minute. The first flow rate can be about 7.5 mL/minute and the second flow rate can be between about 280 mL/minute to about 500 mL/minute.

The system can further include a control module in operative, bi-directional communication with the pneumatic system. The air flow sensor can communicate information regarding a flow rate through the low flow branch to the control module. The control module can communicate with the pump to change a pump speed and alter the flow rate through the low flow branch. Altering the flow rate through the low flow branch can alter a flow rate through the high flow branch. The control module can communicate with the first orifice to change a size of the first orifice and alter the flow rate through the low flow branch. The size of the first orifice can be changed by a valve. The control module can communicate with a plurality of adjustable flow channels extending through the first orifice to change a number of the plurality of adjustable flow channels that are open and alter the flow rate through the low flow branch. The number of the plurality of adjustable flow channels that are open can be changed by a valve. A diameter of the first orifice and a diameter of the second orifice can create a flow ratio between the low flow branch and the high flow branch. The diameter of the first orifice can be between about 0.004 inch and about 0.006 inch and the diameter of the second orifice can be between about 0.009 inch and about 0.012 inch.

The system can further include a filter located in the high flow branch upstream of the second orifice. The system can further include a pressure sensor in the high flow branch downstream of or across the second orifice. No separate pump can be needed to generate a high flow rate for remote sampling using a remote sampling hose coupled to the inlet. The airflow sensor can be a mass airflow sensor. The airflow sensor can be positioned upstream of the first orifice.

In an interrelated aspect, disclosed is a method including drawing an air sample from an atmosphere through an inlet in a housing using a pump contained within the housing; dividing the air sample within the housing into a first portion and a second portion; directing the first portion through a low flow branch towards an analyzer contained within the housing. The analyzer is configured to detect and measure a gas species in the air sample using a gas sensor.

The method can further include sensing a flow rate of the first portion using an airflow sensor located within the low flow branch. The airflow sensor can be a mass airflow sensor. The airflow sensor can be positioned upstream of the first orifice. The method can further include controlling the flow rate of the first portion. Controlling the flow rate of the first portion can include changing a pump speed and altering the flow rate through the low flow branch. Controlling the flow rate of the first portion can include changing a size of the first orifice and altering the flow rate through the low flow branch. Controlling the flow rate of the first portion can include changing a number of flow channels through the first orifice and altering the flow rate through the low flow branch. Altering the flow rate through the low flow branch can alter a flow rate of the second portion. The method can further include directing the second portion through a high flow branch. The high flow branch can have a second orifice. The low flow branch and the high flow branch can each be contained within the housing and in fluid communication with the pump and the inlet. Drawing an air sample can include drawing the air sample using a remote sampling hose coupled to the inlet. Dividing the air sample can include dividing the air sample using a Y or T fitting located in the inlet. The method can further include removing sulfur trioxide and particulates from the air sample using a filter positioned within the low flow branch. The gas sensor can be positioned on a disposable element. A plurality of gas sensors can be positioned on the disposable element as a parallel array. The disposable element can be a planar chip.

Non-transitory computer program products (i.e., physically embodied computer program products) are also described that store instructions, which when executed one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims

DESCRIPTION OF DRAWINGS

FIG. 2 illustrates a top view schematic of an implementation of a gas sensor cartridge for use with the gas detection system of FIG. 1A;

Like reference symbols in the various drawings indicate like elements.

DETAILED DESCRIPTION

Described herein are devices, systems, methods and articles to monitor, detect and analyze various substances, such as gas species, in an environment.

Figure 1A:
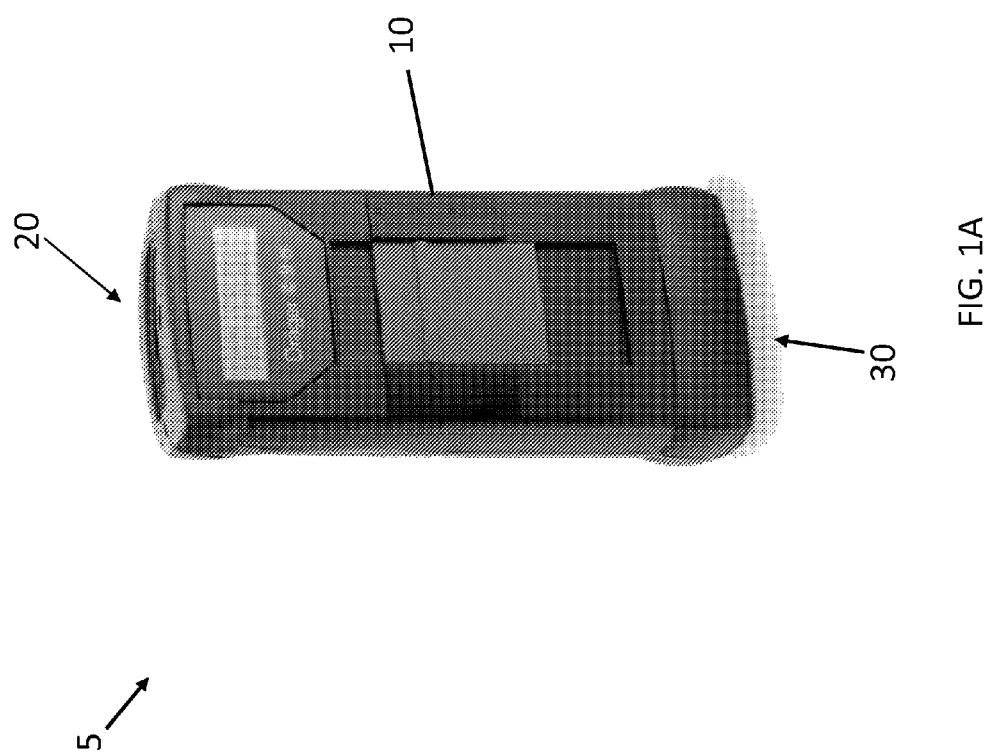
FIG. 1A illustrates a perspective view schematic of an implementation of a gas detection system incorporating a remote sampling bypass.
Figure 1B:
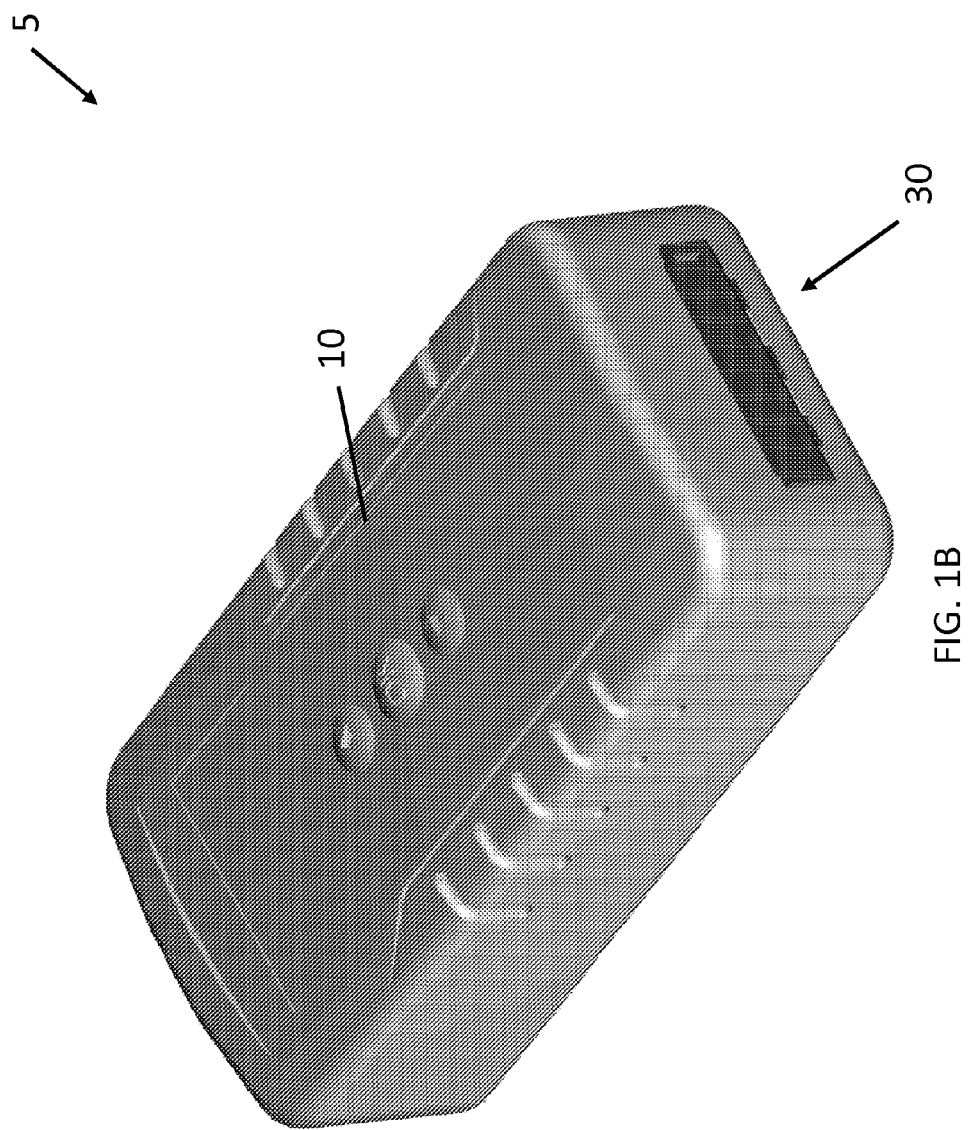
FIG. 1B illustrates an end view of the gas detection system of FIG. 1A.
Figure 1C:
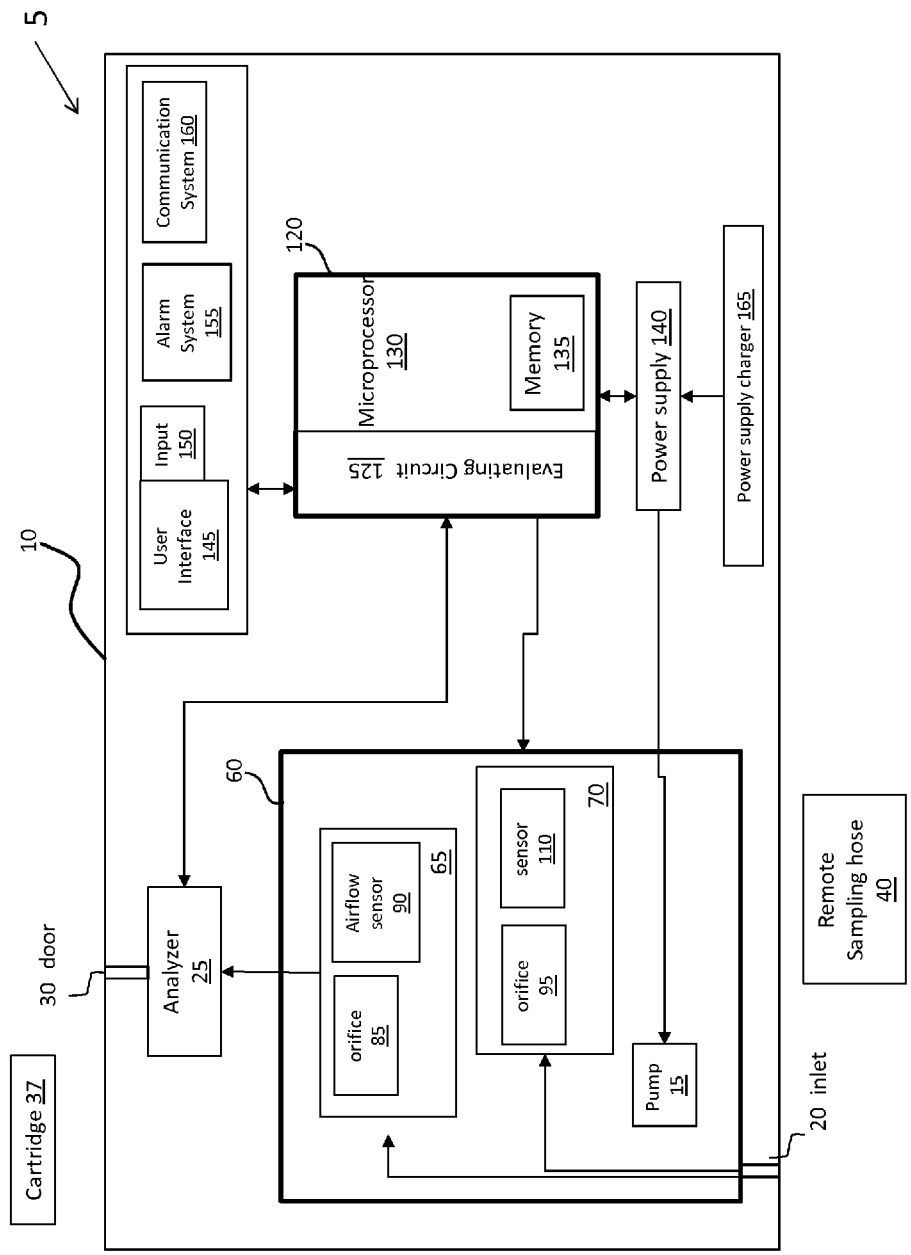
FIG. 1C illustrates a box diagram of the gas detection system of FIG. 1A.

FIGS. 1A, 1B, and 1C illustrate an implementation of a gas detection system 5 having a remote sampling bypass. The system 5 can be used to detect gases using a single pump that creates both a low flow and a high flow path through the system for detection by one or more gas sensors of the system 5. As used herein "gas sensor" can include an element capable of detecting a gas species in an air sample of an atmosphere or environment. The gas sensor can include, but is not limited to an electrochemical gas sensor, a colorimetric gas sensor, infrared detectors, semiconductor sensors, catalytic sensors, photoionization detectors (PID), catalytic bead (pellistor) gas sensor, infrared-optical sensor, galvanic gas sensor, and other types of gas sensor known in the art. The gas detection system 5 can be Chip-Measurement-System (CMS) (Dräagerwerk AG&Co KGaA) in which the gas sensor is contained within a disposable element as will be described in more detail below. It should be appreciated that although the remote sampling bypass is described herein in context of CMS-type monitoring systems and consumable gas sensor cartridges, a variety of gas detection system implementations are considered. For example, the gas detection system 5 can be a real-time continuous gas monitoring system such as the PAC 7000 or X-AM 5600 with OV sensors (Dräagerwerk AG&Co KGaA).

The gas detection systems described herein can be used in a variety of locations, including, but not limited to confined space entry such as shafts, tunnels or tanks, and others, locations of natural gas extraction, production and distribution, factories, petro-chemical production and staging, Marcellus Shale gas extraction and production, drill pad (drilling, fracking and flaring operations, frack water re-use/storage/treatment (VOC release from evaporation, leaks and spills), condensate/collection tanks, compressor station emissions, routine pressure relief gas releases (VOCs, $H_2S$, CO), diesel or gas fueled compressor engine exhaust (NOX, CO, formaldehyde, ozone), Manufacturing /production of chemicals, petrochemical, solvents, adhesives, paints, stains, other coatings, aircraft manufacturing, boat building, car manufacturing, Hazardous Materials ((e.g. toxic, corrosive, explosive) in manufacturing, construction and end-product use, firefighting, Hazmat environments, locations of chemical warfare, or any locations subject to off-gassing. The systems described herein can have application in any area where toxic gases may occur, such as military and law enforcement use as well as in hospitals, research facilities, and industrial facilities to detect exposure to dangerous substances that might be inadvertently released into the environment.

Again with respect to FIG. 1C, the gas detection system 5 can include a housing 10 within which a pump 15 is located. The pump 15 can be in fluid communication with the atmosphere via an inlet 20 in the housing 10. The system 5 can include an analyzer 25 contained within the housing 10 configured to analyze and perform a reading of a gas sensor.

In some implementations, the analyzer 25 is configured to analyze and perform a reading of a gas sensor contained on a gas measurement cartridge 37 also known as a "chip." As shown in FIG. 2, the cartridge 37 can be a disposable element configured to hold one or more gas sensors. The gas sensor of the cartridge 37 can include a gas measurement tube 38 containing reactants such as colorimetric chemicals configured to change color upon exposure to a gas species. Each cartridge 37 can include 1, 2, 3, 4, 5, 6, 7, 8, 9, 10, 12, 15, 20, or more measurement tubes 38. In some implementations, the cartridge 37 can have 10 measurement tubes 38. Each cartridge 37 can include more or fewer measurement tubes 38 and the measurement tubes 38 can be grouped into related subsets of detection. It should be appreciated that any combination of measurement tubes 38 in a cartridge 37 are considered herein. It should also be appreciated that the measurement tube need not be a tube, per se. For example, the reactants can be on a paper carrier.

It should be appreciated that the cartridge 37 can have various configurations. In some implementations, the cartridge 37 can include single and Simulset short term tubes and tube cartridges (Dräagerwerk AG&Co KGaA). The cartridge 37 can, but need not, be a planar element. The measurement tubes 38 can be positioned on the cartridge 37 as a parallel array although it should be appreciated that the cartridge 37 can include a single measurement tube. Each measurement tube 38 within the cartridge 37 can be formed of a variety of transparent materials including, for example, glass or clear plastic or paper. Generally, the measurement tube 38 is a tube of capillary dimension such that gas flow through the measurement tube 38 can occur by capillary action.

Each measurement tube 38 can be configured to detect one of a variety of different gases including, but not limited to, combustible gases, VOC, $NH_3$, $AsH_3$, $CO_2$, CO, $Cl_2$, $C_2H_6$, HCl, HCN, HF, $PH_3$, $H_2S$, $CH_4$, NO, $NO_2$, $O_3$, $O_2$, $C_7H_{16}$, $COCl_2$, $C_3H_8$, $SO_2$, Ammonia, Ethane, Methane, Pentane, and Propane, benzene, toluene, and others depending on the reactants contained within the tube 38. The reactants can be exposed to air sampled from the environment, for example upon insertion of the cartridge 37 into the analyzer 25 through an opening or door 30 in the housing 10. Upon exposure to a particular gas, sand within the measurement tube 38 can change color providing a colorimetric indication of the presence and level of the gas in the environment. The color can indicate exactly what gas is present, how much, and the rate of change. Optics and electronics within the analyzer 25 can perform colorimetry to convert the degree of coloration of the derivative within the measurement tube 38 into a quantitative digital signal.

Figure 3:
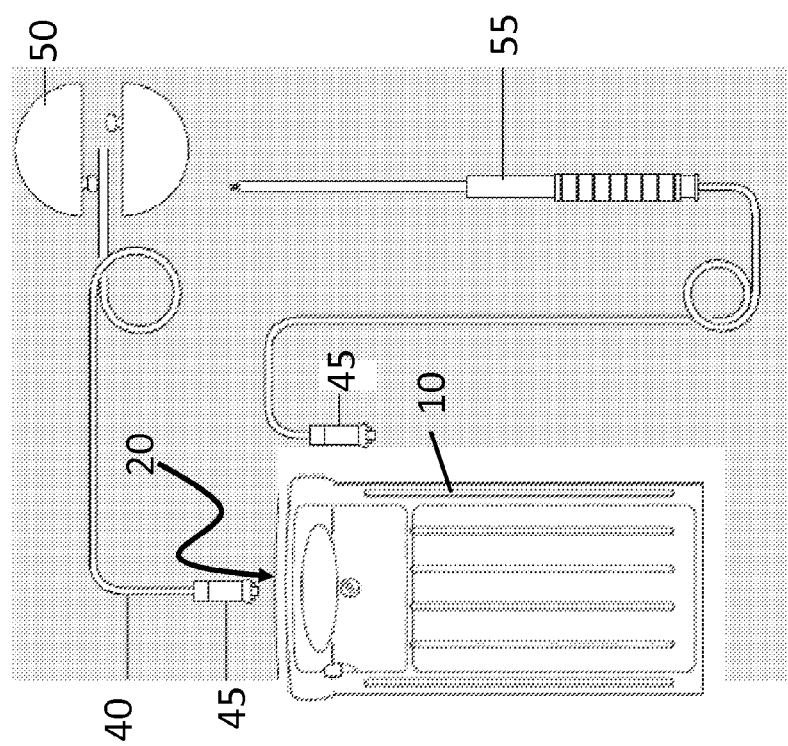
FIG. 3 illustrates remote sampling accessories that can be used with the gas detection system of FIG. 1A.
Figure 4:
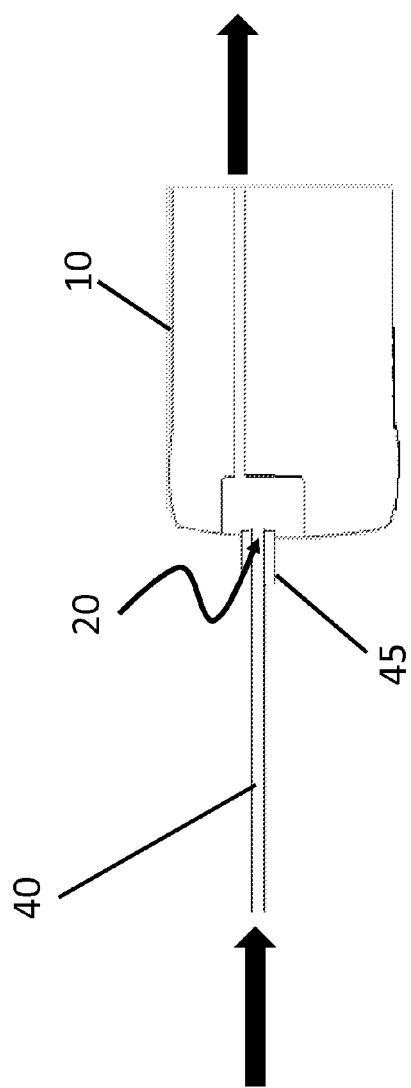
FIG. 4 illustrates a schematic of air flow into the gas detection system of FIG. 1A.

In order for the gas sensor to detect a gas in the environment, such as by a cartridge 37 loaded into the analyzer 25, the pump 15 can draw an air sample from the atmosphere through the inlet 20 into the housing 10 and direct at least a portion of the air sample towards the analyzer 25. It can be desirable to collect an air sample that is remote from the location of the analyzer 25, for example, inaccessible places such as ducts, shafts or tank systems to measure various hazardous gases and vapors that may be present. In such instances, a sampling hose 40 can be connected to the inlet 20 of the housing 10, such as with an adapter 45, to sample the remote atmosphere (see FIGS. 3 and 4). A float 50 or other feature, such as a telescopic tube 55, can be coupled to a distal end of the sampling hose 40 to aid in the collection of the sample, such as an air sample above a liquid surface. The sampling hose 40 can be a variety of lengths depending on the environment for which a measurement is desired. In some implementations, the sampling hose 40 can be up to 5, 10, 15, 20, 25, 30, 35, or more meters long.

A relatively high flow rate can be needed to draw an air sample through a sampling hose 40 of such length. However, a relatively low flow rate can be needed to draw the air sample through a gas sensor, such as a gas sensor on a cartridge 37 loaded in the analyzer 25, to ensure an accurate reading is obtained. Further, gas sensors can have a different resistance to flow, for example depending on what chemicals are present within the measurement tube 38 of the cartridge 37, and can require a particular predetermined flow rate. As will be described in more detail below, the system 5 described herein has a remote sampling bypass that allows an air sample to be drawn from the atmosphere, either locally or remotely, using a pneumatic system 60 having a single pump 15 contained within the housing 10 of the system 5 and in fluid communication with an inlet 20 in the housing 10 to draw an air sample from the atmosphere. One pump can be used to simultaneously achieve the predetermined, low flow rate for the gas measurement portion of the system 5 and the high flow rate needs of the remote sampling system. No separate pump is needed to generate the high flow for the remote sampling.

Figure 5:
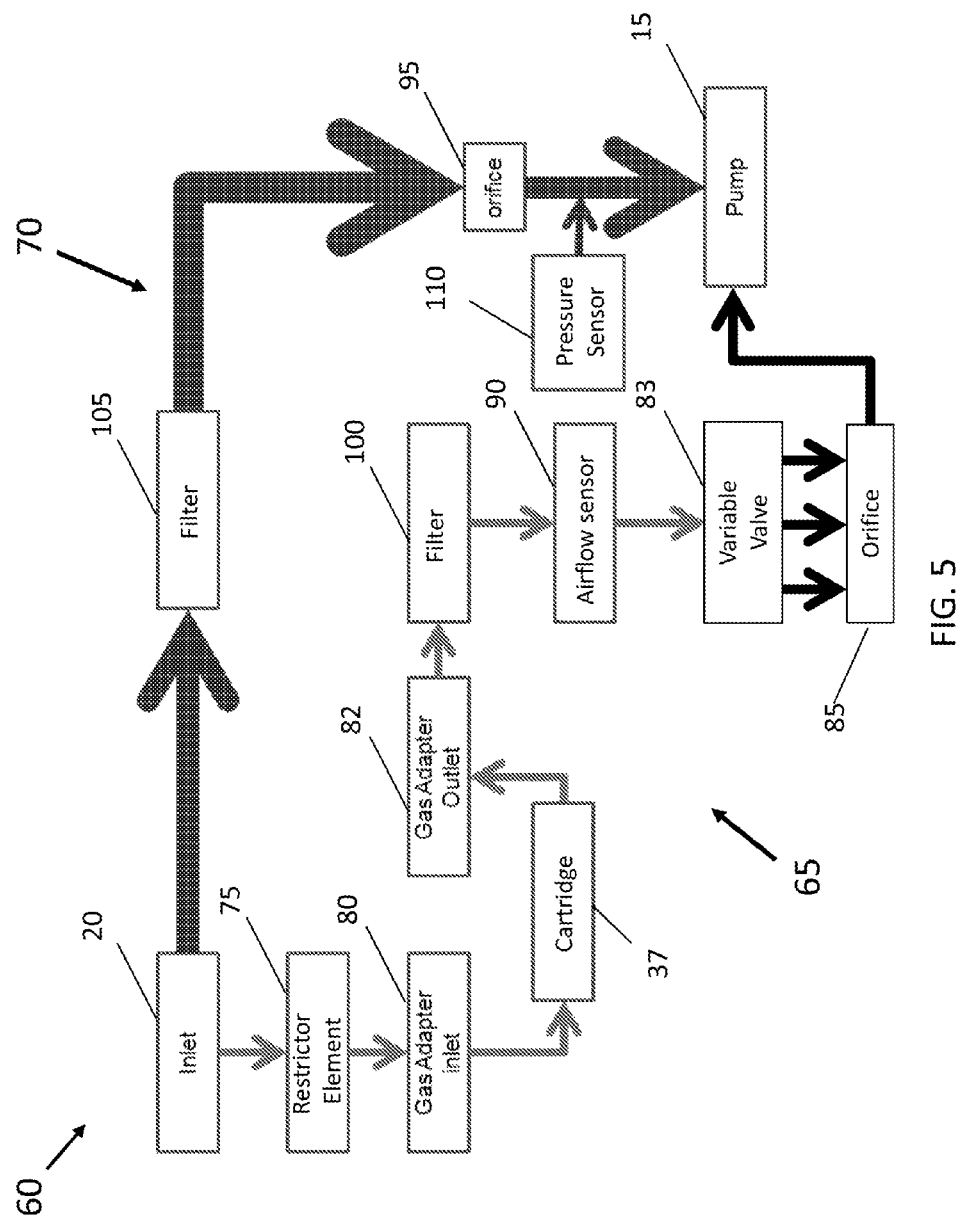
FIG. 5 illustrates a box diagram showing air flow through the remote sampling bypass of the pneumatic system of the gas detection system of FIG. 1A.

As shown in FIG. 5, the pneumatic system 60 of the system 5 can draw an air sample from the atmosphere through the inlet in the housing using the pump 15. The air sample can be divided into two flow branches each in fluid communication with the pump 15, including a low flow branch 65 and a high flow branch 70 which are each drawn by the single pump 15. The pump 15 can include a direct current (DC) powered diaphragm air pump although it should be appreciated that other pump configurations are considered herein. The inlet 20 can include a fitting, such as a Y-, T- or other type of fitting, coupled to it in order to divide the flow into the low flow branch and the high flow branch. The low flow branch 65 can be used to direct the air sample toward the analyzer 25 such that a gas measurement can be performed by a gas sensor, such as a gas sensor on a cartridge 37 loaded within the analyzer 25 as shown in FIG. 5. The high flow branch 70 can be used to draw the air sample via a sampling hose 40 for remote sampling. The pneumatic system 60 can draw the air sample using a single pump 15 to flow the sample at predetermined flow rates. This can eliminate the need for a separate pump coupled to the system 5, such as for drawing a remote sample through the remote sampling hose 40. A single pump system can also reduce the size, weight and/or cost of the system 5 as well as improve battery life.

Again with respect to FIG. 5, the inlet 20 can be an opening in the housing 10 and can be in fluid communication with the atmosphere and the pneumatic system 60. The inlet 20 can include a rubber element for sealing with the adapter 45 such that the remote sampling hose 40 can be coupled to the inlet 20. The inlet 20 can be coupled on a downstream side to a restrictor element 75 within the housing 10. The restrictor element 75 can be a glass tubular element in communication with the inlet 20 and having a specific inner diameter. The inner diameter of the restrictor element 75 can be smaller than the inner diameter of the inlet 20. In some implementations, the restrictor element 75 has a 0.6 mm inner diameter. The restrictor element 75 can be a gas transport tube used to minimize the volume between the inlet 20 and the analyzer 25. By minimizing the volume between the analyzer 25 and the inlet 20, an accurate measurement by the gas sensor contained therein can be obtained, for example by allowing the chemicals within the measurement tube 38 of a cartridge 37 to quickly react with the gas. Further, the restrictor 75 can minimize the amount of gas that remains in the system 5 once the pump 15 stops. It should be appreciated, however, that the single pump system need not include a restrictor element 75.

In some implementations, the cartridge 37 can be inserted into the analyzer 25 of the gas detection system 5 such that the cartridge 37 can be exposed to at least a portion of the air sample drawn by the pump 15 and read by the analyzer 25 such that the presence or an amount of a gas species in the air sample can be detected and measured. An upstream portion of the cartridge 37 can couple with a gas adapter inlet 80 and a downstream portion of the cartridge 37 can couple to a gas adapter outlet 82. This allows for one of the measurement tubes 38 in the cartridge 37 to be exposed to a portion of the air sample. As mentioned above, the resistance to flow through the cartridge 37 can depend on what chemicals are present within the measurement tube 38. As such, each tube 38 can require a particular flow rate therethrough to ensure an accurate exposure of the chemicals to the air sample and to ensure an accurate reading by the analyzer 25.

Still with respect to FIG. 5, the low flow branch 65 can include an airflow sensor 90 such as a mass airflow (MAF) sensor or volume airflow sensor. The airflow sensor 90 can be positioned downstream from the gas adapter outlet 82 and upstream from an orifice 85. It should be appreciated that the airflow sensor 90 can be positioned anywhere within the low flow branch 65. The orifice 85 can be a jeweled restricting orifice. The high flow branch 70 can include an orifice 95 as well. Generally, the diameter of the orifice 85 is between about 0.004 inch and 0.006 inch and the diameter of the orifice 95 is between about 0.009 inch and 0.012 inch. In some implementations, the diameters of the orifices 85, 95 are different. In some implementations, the diameter of the orifice 85 is smaller than the diameter of the orifice 95. In some implementations, the flow ratio between the low flow branch 65 and the high flow branch 70 can be at least about 25:1, 26:1, 27:1, 28:1, 29:1, 30:1, 31:1, 32:1, 33:1, 34:1, 35:1, 36:1, 37:1, or 38:1.

The orifices 85, 95 can create a flow ratio between the low flow branch 65 and the high flow branch 70 to achieve two flow rates. The flow rate of the first portion of the air sample flowing through the low flow branch and the flow rate of the second portion of the air sample flowing through the high flow branch are each controlled by the low flow branch. Air flow through the two-branch pneumatic system 60 can be controlled by the low flow branch 65 such that the high flow branch 70 of the pneumatic system 60 is a function of the flow rate created by the low flow branch 65. For example, if the low flow branch 65 is regulated to 7.5 mL/minute flow rate, then the high flow branch 70 can have a flow rate of approximately 300 mL/minute. The high flow branch 70 can be restricted, but unregulated such that the correct flow can be regulated on the low flow branch 65. In some implementations, the flow rate through the low flow branch 65 can be at least about 7.5 mL/minute, 10 mL/minute, 12.5 mL/minute, 15 mL/minute, and/or 20 mL/minute, and/or 50 mL/minute. In some implementations, the flow rate through the high flow branch 70 can be at least about 280 mL/minute to at least about 500 mL/minute, while the flow rate through the low flow branch 65 is maintained to at least about 7.5 mL/minute, 10 mL/minute, 12.5 mL/minute, 15 mL/minute, 20 mL/minute, or 50 mL/minute. Altering the flow rate through the low flow branch can alter the flow rate through the high flow branch.

The pneumatic system 60 can be in operative, bi-directional communication with a control module 120 (see FIG. 1C). The control module 120 of the gas detection system 5 can be positioned on a printed circuit board and have an evaluating circuit 125 and a microprocessor 130 operatively connected to a memory 135. The airflow sensor 90 of the low flow branch 65 of the pneumatic system 60 can interpret the flow rate through the low flow branch 65 and communicate the information to the control module 120. The control module 120 can, in turn, communicate with one or more components of the pneumatic system 60 to alter flow rates, as described in more detail below.

In some implementations, flow through the pneumatic system 60 can be controlled by changing the speed of the pump 15. For example, the control module 120 can adjust the pulse width modulation (PWM) drive signal controlling the speed of the pump motor to regulate the flow rate through the low flow branch 65 of the pneumatic system 60. Alternatively or additionally, the flow rate through the low flow branch 65 can be adjusted by changing flow through one or both orifices 85, 95. For example, the size of one or both of the orifices 85, 95 can be adjustable such as with a controllable needle valve (e.g., variable valve 83). Alternatively, one or both of the orifices 85, 95 can have a plurality of adjustable flow channels extending therethrough. The flow channels can be opened and closed such as via a solenoid valve to change the number of flow channels through one or both orifices 85, 95 in order to achieve a particular ratio and flow rate. It should be appreciated that any number of configurations are considered herein to regulate the flow through the low flow branch 65 and/or the high flow branch 70.

The control module 120 can also be in operative bi-directional communication with the analyzer 25. In some implementations, an information element 39 can be positioned on the cartridge 37 (see FIG. 2). The information element 39 can be configured to be scanned and read by a reader device such as upon loading the cartridge 37 within the analyzer 25. The information element 39 can be a radiofrequency identification ("RFID") tag, an optical code such as a two-dimensional bar code, three-dimensional bar code or the like. Data stored within the information element 39 can be communicated to the control module 120 and can include a variety of information regarding the cartridge 37 and the measurement tubes 38 present on the cartridge 37, including, but not limited to identification of the cartridge 37, type of measurement tube 38, settings or adjustment of certain parameters for proper use of the cartridge 37 such as flow rate through the measurement tube 38. The control module 120, in turn, can automatically adjust the flow rate through the cartridge 37 to the optimum flow rate for that particular cartridge 37 or measurement tube 38. It should be appreciated that each tube 38 on a single cartridge 37 can have different chemicals contained in them and different optimum flow rate parameters. Alternatively, all the tubes 38 of a single cartridge 37 can have the same chemicals and identical flow rate parameters.

Again with respect to FIG. 5, the pneumatic system 60 can incorporate one or more filters in the low flow branch 65 as well as the high flow branch 70. In some implementations, the low flow branch 65 of the pneumatic system 60 can include a filter 100 such as a sulfur trioxide ($SO_3$)/particulate filter positioned downstream of the inlet 20 and upstream of the airflow sensor 90 and the orifice 85. The filter 100 can protect the airflow sensor 90 and the pump 15 from dust, water, $SO_3$, and other impurities. The pneumatic system 60 can also incorporate one or more filters 105 within the high flow branch 70 upstream of the orifice 95 and the pump 15 to remove impurities from the high flow branch 70. Further, the high flow branch 70 can include a pressure sensor 110 positioned downstream of the orifice 95 and upstream of the pump 15. The pressure sensor 110 can be used to determine if the high flow branch 70 has become restricted.

Again with respect to FIG. 1C, the gas detection system 5 can also include a power supply 140, user interface 145 having one or more inputs 150, alarm system 155, and communication system 160 in bi-directional communication with the control module 120. The control module 120 is configured to receive, process, store and command the various components of the system 5 during operation. The control module 120 can run one or more software programs to oversee, manage, and/or coordinate the measurement, evaluation and analysis functions of the analyzer to make the data acquired useful for a user in terms of analysis and reporting. The control module 120 can combine data for logging and analysis. The control module 120 can also use its evaluating circuit 125 to perform periodic system housekeeping functions and self-tests.

As mentioned above, the control module 120 can include a memory 135 that can store electronic data such as flow rates, substance(s) measured, concentration, date and time measured, trend data, temperature compensation, site of measurement, number, calibration values, measure range, cartridge identification information, alarms triggered, alerts, and any other information related to the system 5, its components and their use. The stored data can be retrieved again at any time and communicated to the user such as via the user interface 145. The electronic data capacity of the memory 135 can vary. The electronic data capacity can hold the results of a variety of measurements, including 1, 2, 3, 4, 5, 6, 7, 8, 9, 10, 20, 30, 50, 60, or more measurements, together with relevant data. The memory 135 can be volatile and non-volatile, and removable and non-removable. The memory 135 can include computer storage media, including by not limited to RAM, ROM, EEPROM, flash memory or other memory technology, CD-ROM, DVD, or other optical disk storage, or any other medium which can be used to store computer-readable instructions, software, data structures, program modules, and other data which can be accessed by the system 5. Data can be accessed directly or through a network such as the internet, WAN or a LAN.

The user interface 145 can include a visual information display such as an LCD (liquid crystal display), LED, plasma screen, or a CRT (cathode ray tube) for displaying information to the user such as a reading performed or other information. The one or more inputs 150 of the system 5 can allow the user to provide input to the circuitry. The input 150 can be received in any form, including acoustic, speech, or tactile input. The input 150 can include a user-friendly, mechanical control devices (e.g. switches, dials, keys, buttons), electrical arrangements (e.g. slider, touch screen), wireless interfaces for communication with a remote controller (e.g. RF, infrared), acoustic interfaces (e.g., with speech recognition), computer network interfaces (e.g., USB port), and other types of interfaces. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. The input 150 can be used to selectively activate the power supply 140 during a period of interest.

The power supply 140 can include a variety of types such as one or more batteries, including disposable or rechargeable battery such as a NiCad battery, LiPo battery, Lithium ion battery, NiMH battery or the like. The user interface 145 can indicate the charge of the device if powered by a battery. The system 5 can connect to a power supply charger 165. The power supply charger 165 can include a docking station that provides a constant trickle charge to the power supply 140 provided by, for example, direct connection to a high capacity lead gel battery or a power supply/charger in lieu of a conventional cradle or wall adaptor recharging station.

The system 5 can periodically perform one or more self-checks to verify the readiness and integrity of various components of the system; the external communication links with network peers and/or remote client/supervisors; viability of the analyzer 25 and cartridge 37 loaded; battery remaining charge; configuration whether to allow operation if connected to a battery charging circuit; whether or not the remote sampling hose 40 is coupled to the inlet 20; and others.

The alarm system 155 can include measurement alarms (e.g. threshold alarm etc.) and system alarms (e.g. cartridge jammed/loaded improperly, battery low, etc.). The alarm system 155 can include any form of sensory feedback or alarm (e.g., audible, tactile and/or visual feedback). The alarm system 155 can include one or more illuminated LEDs that indicate a particular status of the system 5 and/or the ambient air condition. In some implementations, the LED can illuminate a green color indicating a clean condition of the ambient air upon taking a measurement. Upon detection of a gas hazard, the LED color can change from green to red. It should be appreciated that other visual warnings can be incorporated. Similarly, a variety of audible warnings or alarms can be incorporated in the system 5 such as through a speaker. It should be appreciated that the alarm system 155 can also cause a wireless signal (e.g. a wireless transmission to a remote controller or monitor) to be transmitted by the communication system 160. The system 5 can also connect to and operate external alarm equipment such as alarm horns, lamps, traffic lights, etc. remote from the system 5. A triple alarm can also be used in which an audible, visual and tactile alarm can be emitted when the threshold is exceeded or a value falls below a configured concentration. The alarm system 155 can be adjustable such that there are one or more alarm set points for a selected measuring range. The alarms can be latching, meaning human intervention is needed for the alarm indication to be reset. The alarm system 155 can generate one or more alarms using multiple mechanisms simultaneously, concurrently or in a sequence, including redundant mechanisms or complementary mechanisms. It should be appreciated that a variety of alarms can be incorporated into the system.

The communication system 160 can be an external communication system configured to send data and hazardous event notifications from the system 5 to an external destination or device and vice versa. The communication system 160 can be used to transmit data such as from the memory 135 to a remote location and/or receive data from remote location device. The system 5 in turn can provide real-time warnings of substances detected in an area. The communication system 160 can transmit via various communications protocols including SMS/MMS to individuals within the monitored area as well as to supervisors/control centers overseeing the activities of such individuals. Other notifications can be delivered by other means including voice telephone calls, e-mails, and the like. The data can be downloaded through the communication system 160 to a remote or local PC, laptop, table computer, smartphone, communication station, another detector system, or other remote device, over a variety of communication lines. The communication system 160 of the system 5 can have wired and/or wireless communication capability such as for the sending and receiving of data as is known in the art. The wireless communication capability can vary including, e.g. transmitter and/or receiver, radiofrequency (RF) transceiver, WTI connection, infrared, optical or Bluetooth communication device, and the like. The wired communication capability can vary including, e.g. USB or SD port, flash drive port, disk, data stick, or the like. The wired and wireless capability may be used for a variety of purposes, including updating software or firmware for the processor.

The system 5 can be suitable for both mobile and stationary use. In some implementations, the system 5 can be a portable or mobile system, such as a hand-held system or a system capable of being carried by a person of ordinary strength. The system 5 can be small enough to be clipped onto or held by a person, such as on a belt or piece of clothing using a clip accessory coupled to a portion of the housing 10 or in a pocket in the person's clothing. Alternatively, the system 5 can be held and transported using a handle coupled to a portion of the housing 10.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal. The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A gas detection system comprising:
   a housing having an inlet in fluid communication with an atmosphere;
   an analyzer within the housing and configured to detect and measure a gas species in the atmosphere using a gas sensor; and
   a pneumatic system contained within the housing and in fluid communication with the inlet to draw an air sample from the atmosphere, the pneumatic system comprising:
      a pump;
      a low flow branch in fluid communication with the pump and having an airflow sensor and a first orifice; and
      a high flow branch in fluid communication with the pump and having a second orifice
   wherein:
      the air sample is divided into a first portion that flows through the low flow branch and a second portion that flows through the high flow branch,
      air flow through the pneumatic system is controlled by the low flow branch such that a flow rate in the high flow branch of the pneumatic system is a function of the flow rate created by the low flow branch, and
      a diameter of the first orifice and a diameter of the second orifice create a flow ratio between the low flow branch and the high flow branch.

2. The system of claim 1, further comprising a filter upstream of the airflow sensor.

3. The system of claim 2, wherein the filter is a sulfur trioxide particulate filter.

4. The system of claim 1, further comprising a remote sampling hose connected to the inlet to enable sampling of at least a portion of the air sample within the high flow branch remotely.

5. The system of claim 4, wherein the pump is configured to draw the air sample through the remote sampling hose using the high flow branch.

6. The system of claim 1, wherein the first portion flows through the gas sensor.

7. The system of claim 1, wherein the gas sensor is positioned on a disposable element.

8. The system of claim 7, wherein a plurality of gas sensors are positioned on the disposable element as a parallel array.

9. The system of claim 7, wherein the disposable element is a planar chip.

10. The system of claim 1, wherein a first flow rate of the first portion and a second flow rate of the second portion are each controlled by the low flow branch.

11. The system of claim 10, wherein the first flow rate is at least about 7.5 mL/minute, 10 mL/minute, 12.5 mL/minute, 15 mL/minute, 20 mL/minute, or 50 mL/minute.

12. The system of claim 10, wherein the first flow rate is about 7.5 mL/minute and the second flow rate is between about 280 mL/minute to about 500 mL/minute.

13. The system of claim 1, further comprising a control module in operative, bi-directional communication with the pneumatic system.

14. The system of claim 13, wherein the air flow sensor communicates information regarding a flow rate through the low flow branch to the control module.

15. The system of claim 13, wherein the control module communicates with the pump to change a pump speed and alter the flow rate through the low flow branch.

16. The system of claim 15, wherein altering the flow rate through the low flow branch alters a flow rate through the high flow branch.

17. The system of claim 1, wherein the control module communicates with the first orifice in the low flow branch to change a size of the first orifice and alter the flow rate through the low flow branch.

18. The system of claim 17, wherein the size of the first orifice is changed by a valve.

19. The system of claim 1, wherein the control module communicates with a plurality of adjustable flow channels extending through the first orifice to change a number of the plurality of adjustable flow channels that are open and alter the flow rate through the low flow branch.

20. The system of claim 19, wherein the number of the plurality of adjustable flow channels that are open is changed by a valve.

21. The system of claim 1, wherein the diameter of the first orifice is between about 0.004 inch and about 0.006 inch and wherein the diameter of the second orifice is between about 0.009 inch and about 0.012 inch.

22. The system of claim 1, further comprising a filter located in the high flow branch upstream of the second orifice.

23. The system of claim 1, further comprising a pressure sensor in the high flow branch downstream of or across the second orifice.

24. The system of claim 1, wherein no separate pump is needed to generate a high flow rate for remote sampling using a remote sampling hose coupled to the inlet.

25. The system of claim 1, wherein the airflow sensor is a mass airflow sensor.

26. The system of claim 1, wherein the airflow sensor is positioned upstream of the first orifice.

27. A method comprising:
    drawing an air sample from an atmosphere through an inlet in a housing using a pump contained within the housing;
    dividing the air sample within the housing into a first portion and a second portion;
    directing the first portion through a low flow branch of a pneumatic system towards an analyzer contained within the housing, the analyzer configured to detect and measure a gas species in the air sample using a gas sensor, the low flow branch having a first orifice; and
    directing the second portion through a high flow branch of the pneumatic system, the high flow branch having a second orifice;
        wherein altering a flow rate through the low flow branch alters a flow rate of the second portion, and
        wherein a diameter of the first orifice and a diameter of the second orifice create a flow ratio between the low flow branch and the high flow branch.

28. The method of claim 27, further comprising sensing the flow rate of the first portion using an airflow sensor located within the low flow branch.

29. The method of claim 28, wherein the airflow sensor is positioned upstream of the first orifice in the low flow branch.

30. The method of claim 27, further comprising controlling the flow rate of the first portion.

31. The method of claim 30, wherein controlling comprises changing a pump speed and altering the flow rate through the low flow branch.

32. The method of claim 30, wherein controlling comprises changing a size of the first orifice and altering the flow rate through the low flow branch.

33. The method of claim 30, wherein controlling comprises changing a number of flow channels through the first orifice and altering the flow rate through the low flow branch.

34. The method of claim 27, wherein the low flow branch and the high flow branch are each contained within the housing and in fluid communication with the pump and the inlet.

* * * * *